United States Patent [19]

Biller

[11] 4,297,511
[45] Oct. 27, 1981

[54] METHOD FOR THE MANUFACTURE OF POLYARYLAMINES HAVING METHYLENE BRIDGES

[75] Inventor: Efim Biller, Zurich, Switzerland

[73] Assignee: Sulzer Brothers Limited, Winterthur, Switzerland

[21] Appl. No.: 72,313

[22] Filed: Sep. 4, 1979

[30] Foreign Application Priority Data

Sep. 12, 1978 [CH] Switzerland ............... 9537/78

[51] Int. Cl.³ ............................................. C07C 87/28
[52] U.S. Cl. ...................................... 564/331; 564/334
[58] Field of Search ................. 260/570 D; 564/331, 564/334

[56] References Cited

U.S. PATENT DOCUMENTS

| | | | |
|---|---|---|---|
| 3,931,320 | 1/1976 | Eifler et al. | 260/570 D |
| 3,954,867 | 5/1976 | Funk et al. | 260/570 D |
| 3,996,283 | 12/1976 | Knöfel | 260/570 D |
| 4,025,557 | 5/1977 | Eifler et al. | 260/570 D |
| 4,061,678 | 12/1977 | Knöfel et al. | 260/570 D |
| 4,087,459 | 2/1978 | Knöfel et al. | 260/570 D |
| 4,130,588 | 12/1978 | Martin et al. | 260/570 D |

*Primary Examiner*—Paul F. Shaver
*Attorney, Agent, or Firm*—Kenyon & Kenyon

[57] ABSTRACT

Through condensation ortho- and para-isomers of methylene dianiline (MDA) as well as PMPPA are produced as condensation products from arylamines, especially from aniline, and formaldehyde in the presence of acid catalysts, in which at least one component is a perfluoro-carbonic acid. From this mixture of the condensation products, 4,4'-MDA (p-isomer) of high purity is obtained by crystallization while the homogeneous aqueous solution obtained is being cooled down. It has been discovered that the 4,4'-MDA salts of the perfluoro-carbonic acids are less soluble in water than the corresponding salts of the o-isomers and the PMPPA.

16 Claims, 1 Drawing Figure

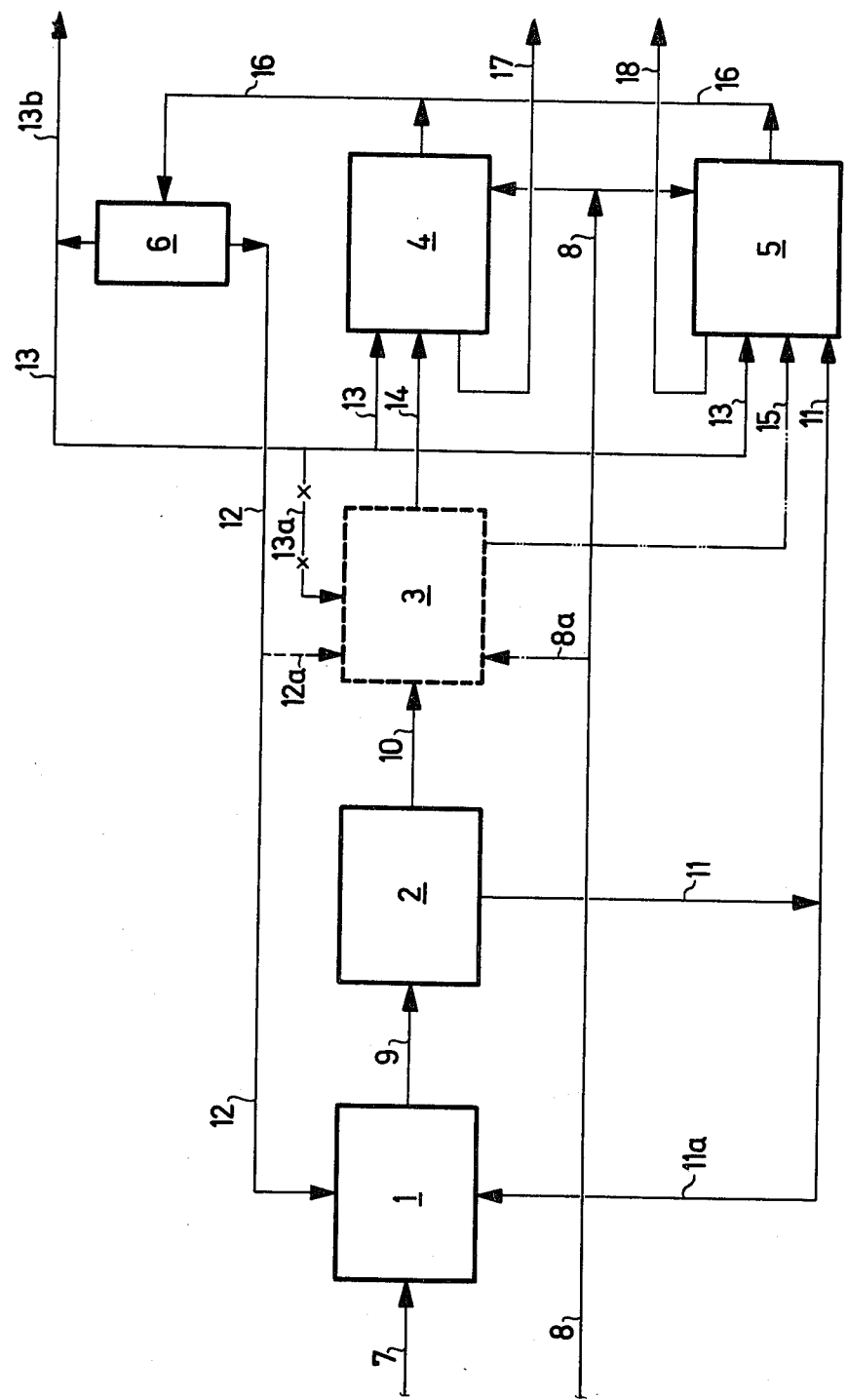

METHOD FOR THE MANUFACTURE OF POLYARYLAMINES HAVING METHYLENE BRIDGES

The invention relates to a method for the simultaneous production of pure 4,4'-methylene diarylamine (MDA) and polyamines which have methylene bridges.

Monomeric 4,4'-methylene diarylamine (MDA) is an important intermediate for the production of polyamides and of chain extenders for polyurethanes, 4,4'-methylene diisocyanate and others.

Polyamines having methylene bridges are, as known, a mixture of monomeric MDA and polymethylene polyphenylene amines (PMPPA); in polyamines a high 4,4'-MDA content—preferably more than 90% (all percents are % in weight) of the monomeric share—is required. The manufacture of these polyamines (PA) as well as the conversion of such compounds into corresponding polyphenylpolyisocyanates having methylene bridges is generally known. The polyisocyanates are frequently used as intermediate products for the manufacture of polyurethanes in the form of, for instance, rigid foams, cast plastic products and elastomers.

In polyurethane chemistry, polyisocyanate mixtures of the diphenyl methane series represent particularly valuable raw materials which are distinguished by a high content—more than 90%—of 4,4'-diisocyanate diphenyl methane and a small content of o-isomers such as, for instance, 2,2'-or 2,4'-diisocyanate diphenyl methane. The 2,2'- or 2,4'-isomer content of the polyamine mixtures is primarily a function of the strength and concentration of the acid catalyst used. A high degree of protonization (degree of protonization is the percentage of the total quantity of amino groups which are present as ammonium groups) generally leads to an increased para-isomer content of the condensation products.

It is further known that the aniline salts of methanesulfonic acid do not dissolve very well in water. For instance, a 55-% solution, i.e., 55% by weight aniline salt dissolved in 45% water, crystallizes out already at 60° C. to 65° C. The aniline salts of trifluoro-acetic acid (TFE), on the other hand, are highly soluble in water.

Surprisingly, it has now been found that in contrast thereto, the salts of methylene-dianiline (MDA) isomers of trifluoroacetic acid are only slightly soluble or not at all in water at temperatures below 60° C. The MDA salts of methanesulfonic acid (MSS), on the other hand, are highly soluble in water at room temperature. The MDA salts of a mixture of TFE and MSS exhibit a similar behavior as those of pure TFE; the crystallization temperature drops with increasing MSS content.

It has been found that the salts of 4,4'-MDA (para-isomer) are less soluble in water or salt/water mixtures than those of the ortho-isomers (2,2'-and 2,4') and of the PMPPA.

Due to these new discoveries, it is possible to improve the purity of 4,4'-methylene dianiline which is obtained from condensation mixtures of aniline and formaldehyde in the presence of perfluoro-carbonic acids, especially of TFE or their mixtures with strong acids having a pKa value below 2,5 especially organic sulfonic acids, e.g. MSS.

Accordingly, it is an object of the invention to obtain 4,4'-methylene-dianiline of the highest possible purity.

Another object of the invention is to obtain polyamines, as defined, with high 4,4'-MDA content in the monomeric share. Briefly, the invention provides a method of making pure 4,4'-MDA and polyamines which comprises the steps of condensing formaldehyde with at least 40% protonized aniline salt solution containing at least perfluoro-carbonic acid to obtain a homogeneous aqueous solution and cooling the homogeneous solution in a given temperature range to crystallize and precipitate 4,4'-methylene diarylamine as a salt and to leave substantially the other condensed arylamines as salts in the residual liquid.

The aqueous aniline salt solution may also contain a mixture of the perfluoro-carbonic acid and a strong acid having a pKa value below 2.5, such as an organic sulfonic acid. As is well known, the pKa value is understood to mean that pH value at which an acid is 50% dissociated. This value is a measure for the strength of an acid.

The crystals which are precipitated exhibit a high 4,4'-MDA content. The radical of TFE or a mixture of TFE and MSS has been found to be particularly advantageous as acid radicals for these salts.

The degree of protonization of the aniline salt solution influences the yield of the crystallization; therefore it is desirable to adjust selected values of this degree. This may be achieved by extracting non protonized aryl-amines by means of hydrophobic solvents—such as chlorobenzene, o-dichchlorobenzene, toluolene, xylenes and others—before the crystallization takes place. The salt crystals as well as the mother liquor are worked up according to known methods of the art.

It has been found that an addition of non-protonized aniline improves the solubility of the salts in water, but that the aniline salts of TFE or the mixture TFE/MSS influence the solubility little. By washing and/or recrystallization (with or from water or aniline salt solution which are present in the condensation process), practically any purity of 4,4'-MDA can be achieved.

As already mentioned, a perfluoro-carbonic acid, especially TFE, alone or in a mixture with other strong acids, having pKa-values below 2.5, is used as the only or at least one acid catalyst in the method. Examples of strong acids which can be used for forming such mixtures are hydrochloric acid, sulfuric acid, hydrobromic acid, as well as organic sulfonic acid, especially methane sulfonic acid or ethane sulfonic acid. Of the acids mentioned, the alkane sulfonic acids are preferred, since their aqueous arylamine salt solutions do not attack the commercially available chromenickel steels.

The method furthermore allows a reduction in the loading of exchanger or reprocessing units following condensation when operating with a larger arylamine excess and a higher degree of protonization, since the residual liquid or mother liquor contains the excess starting arylamine salts as the main products. The possibility is also provided in that crystallization can be used to vary and determine the quality of the finished products, i.e., especially the purity of the 4,4'-MDA, within wide limits without a large amount of technical means. Further, the method can be operated continuously as well as intermittently (batch mode).

These and other objects and advantages of the invention will become more apparent from the following detailed description and appended claims in conjunction with the accompanying drawings in which:

The sole FIGURE shows a process flow diagram for the manufacture of 4,4'-MDA of maximum purity.

Referring to the drawing, in order to obtain a polyarylamine, condensation of the initial arylamine, for example aniline, into di- and polyamines takes place in condensation chamber 1. For this purpose, a flow of formaldehyde is delivered via a line 7 to the chamber 1 while a concentrated aqueous solution of aniline salts with acid radicals of a mixture of TFE and MSS is delivered via a line 12.

After condensation takes place, the obtained homogeneous solution is passed via a line 9 to a crystallization chamber or stage 2 in which single- or multiple-stage crystallization, achieved by simply lowering the temperature, of part of the condensation product takes place. The crystals, which consist predominantly of the desired 4,4'-MDA salt, flow via line 10 to a further treatment stage 3, which is not absolutely necessary but is advantageous for the purity of the 4,4' product.

In some cases, residual liquid of the condensation products which flow from the condensation chamber 1 via the line 9 to the crystallization chamber 2 and which, after the 4,4'-MDA salt has crystallized out as the preferred product in the crystallization chamber 2, contains essentially o-isomers of the MDA salts and the salts of the PMPPA may be returned via a line 11a to the condensation chamber 1. This recycling of the residual liquid subjects at least part of the o-isomers of the MDA salts to condensation with aniline and formaldehyde again, in order to increase the content of polyamines which can be used as a foam material.

The inflowing 4,4'-MDA salt crystals to the treatment stage 3 are washed and/or dissolved and recrystallized, while water is added via a line 13a, initial aniline salt solution via a line 12a and/or aniline via a line 8, 8a.

From the treatment stage 3, the purified crystals are fed, via a line 14, to an exchange facility 4, in which they are processed in accordance with U.S. Ser. No. 914,814, filed June 12, 1978 corresponding to DE-OS 26 48 982, while water is being added via a line 13 and aniline, which is fed to facility 4, is added via a line 8.

The washing liquor or the residual liquid, respectively, which is again enriched with o-isomers or polyamines, arrives via a line 15 at a second similar exchange facility 5, to which also part of the residual liquid or mother liquor flows from the crystallization stage 2 via the line 11. In this facility 5, the residual liquid and the washing liquor are processed in the same manner as the 4,4'-MDA salt in facility 4.

In the above mentioned processing, the 4,4'-MDA and the isomeric 2,2'-and 2,4'-MDA salts and/or the PMPPM salts are separated from the acid radicals to which they are bound chemically, and carried off as the end product via lines 17, 18, respectively. The diluted acid radicals, bound to aniline by the exchange, pass via a line 16 into a common evaporator 6 in which the aniline salt solutions are concentrated before being returned via the line 12 to the condensation chamber 1.

The water evaporated in this process leaves the plant either via a line 13b or is likewise returned and fed to the treatment stages 3, 4 and/or 5 via the different lines 13.

The following example shows for a constant aniline/-formaldehyde ratio the influence of the mixing ratio of the acid catalysts (by the example of TFE and MSS) on the crystallization temperature and the crystal yield as well as the composition of the crystal mixtures obtained from the condensation products.

EXAMPLE I

In three double-walled vessels, each provided with a thermostat, the following is presented to obtain mixing ratios:

| A | B | C |
|---|---|---|
| MSS/TFE 3:1 | MSS/TFE 1:3 | Pure TFE |
| 93 g Aniline | 93 g Aniline | 93 g Aniline |
| 28.2 g TFE | 85.5 g TFE | 114 g TFE |
| 103 g 70% MSS | 34.2 g 70% MSS | 169 g $H_2O$ |
| 106.3 g $H_2O$ | 155.8 g $H_2O$ | |

Each of the vessels thereby contains homogeneous solutions with a salt content of 55% by weight and a water content of 45% by weight; the vessels being maintained at a temperature of 40° C.

In each of these salt solutions, the initial aniline was protonized 100%. Into each of the vessels were added at the temperatures mentioned, 20.27 g (0.25 mol) formaldehyde in the form of a 37-% aqueous solution so that the mole ratio between the aniline and the formaldehyde was 4:1. Subsequently, the mixture was allowed to react about 30 minutes at 50° C., about 30 minutes at 70° C. and about 1 hour at 90° C.

Thereupon the solutions of the products which were generated in this condensation and consist of p-and o-MDA-isomers as well as PMPPA were cooled. During the cooling-down, crystals began to be precipitated at crystallization temperatures of:

| | A | B | C |
|---|---|---|---|
| approx | 27° C. | 38° C. | 50° C. | crystal yields (in grams) being obtained as follows:

| A | B | C |
|---|---|---|
| 97 g | 109 g | 111.4 g |

After the crystals were neutralized with sodium hydroxide (NaOH) (performed in the laboratory instead of by the exchange process described in connection with the drawing), the following composition is obtained:

| A | B | C | |
|---|---|---|---|
| 96,2 | 95,5 | 93,5% | 4,4'-MDA |
| 0,7 | 0,6 | 0,5% | 2,4'-MDA |
| 3,1 | 4,9 | 6,0% | PMPPA |

While the crystal yield also increases with increasing TFE content, as was to be expected, the 4,4'-MDA content in the monomeric share is practically not influenced by changes in the mixing ratio of the two acids used.

In a second example the influence of the aniline/formaldehyde ratio on the ratio of the o- to the p-contents of the MDA was to be determined with the composition of the acid catalyst being constant, i.e., for constant TFE-to-MSS ratio.

EXAMPLE II

In each of the three double-walled vessels, again equipped with thermostats, the following mixing ratios were used:
93 g (1 mol) aniline
57 g (0.5 mol) TFE
68.5 g (0.5 mol) MSS 70%
141.5 g $H_2O$ which again furnishes 55-% aqueous homogeneous salt solutions. To these 100% protonized mixtures the following amounts of formaldehyde in the form of a 37-% aqueous solution were again added at 40° C.:

| A | B | C |
|---|---|---|
| 20.25 g | 28.3 g | 35.45 g |

The mol ratio between aniline and formaldehyde is therefore:

| A | B | C |
|---|---|---|
| 4:1 | 2.85:1 | 2.22:1 |

After the formaldehyde is added, the solutions were treated as in Example 1.

In cooling-down, the following were found as crystallization points, at which the first crystals were visibly precipitated:

| A | B | C |
|---|---|---|
| 28° C. | 29° C. | 31° C. |

After the precipitation was complete, the following crystal yields were obtained as final yields:

| A | B | C |
|---|---|---|
| 60 g | 64 g | 112 g |

An analysis of the crystals similar to Example 1 yielded:

| A | B | C |
|---|---|---|
| 97,6 % 4,4'- | 94,0 % 4,4'- | 87 % 4,4'-MDA |
| 0,4 % 2,4'- | 0,5 % 2,4'- | 0,8 % 2,4'-MDA |
| 2,0 % | 5,5 % | 12,2 % PMPPA |

A slight decrease in 4,4'-MDA is therefore found with increasing formaldehyde content while the PMPPA content is increased at the same time.

EXAMPLE III (Increasing the 4,4'-MDA content in the crystals by means of recrystallization in homogeneous aqueous solution.) The crystals of the example 2C are dissolved in an equal amount of water and heated up to 85° C.; the homogeneous solution is cooled down to 40° C. and the obtained crystals are separeted from the liquid.

An analysis of the crystals worked up similar to Example I:
96,3% 4,4'-MDA
0,2% 2,4'-MDA
3,5% PMPPA

EXAMPLE IV (Yield on the basis of the used aniline.)

3387 g water, 2280 g TFE (20 moles) and 1860 g aniline (20 moles) are condensed with 405 g formaldehyde (5 moles) in the form of a 37% aqueous solution (1 hour at 50° C.; 1 hour at 70° C.; 1 hour at 90° C.). The homogeneous solution is cooled down to 40° C. and the crystals are precipitated during 30 min. The separation of the crystals is done by centrifuging.

1630 g crystals and
6285 g mother liquor are obtained.

After neutralization and washing the following yields are obtained:
From the crystals:
450 g product with 93,2% monomeric MDA
and thereof:
99,5% 4,4'-MDA
6,8% PMPPA.
From the mother liquor:
460 g product with
68,0% monomeric MDA
and thereof:
93,2% 4,4'-MDA
32,0% PMPPA.

The yield corresponds to more than 98% related to the aniline used.

What is claimed is:

1. A method of making simultaneously monomeric 4,4'-methylene diarylamine and polyamines which comprises the steps of
    condensing formaldehyde with a highly protonized aniline salt solution containing at least perfluorocarbonic acid to obtain a homogeneous aqueous solution; and
    cooling the homogeneous solution in a given temperature range to crystallize and precipitate 4,4'-methylene diarylamine as a salt and to leave substantially the other condensed arylamines as salts in the residual liquid.

2. A method as set forth in claim 1 wherein the precipitated salt crystals are worked up to practically pure 4,4'-methylene diarylamine.

3. A method as set forth in claim 1 wherein the mother liquor is worked up to polyamines containing methylene bridges.

4. A method as set forth in claim 1 wherein the aniline salt solution contains a strong acid with a pKa value below 2.5 in mixture with the perfluoro-carbonic acid.

5. A method as set forth in claim 1 wherein said temperature range is between 0° C. and 80° C. depending on the acid mixture and degree of protonization.

6. A method as set forth in claim 5 wherein the degree of protonization is between 40% and 100%.

7. A method as set forth in claim 6 wherein the degree of protonization is between 70% and 100%.

8. A method as set forth in claim 5 wherein said temperature range is between 20° C. and 50° C.

9. A method as set forth in claim 4 wherein the strong acid in the mixture is an organic sulfonic acid preferably methane sulfonic acid.

10. A method as set forth in claim 4 wherein the perfluorocarbonic acid in the mixture is trifluoro-acetic acid.

11. A method as set forth in claim 1 further comprising the step of washing the precipitated crystals with water, eventually adding arylamine thereto.

12. A method as set forth in claim 11 wherein said crystallization and washings steps are performed in several stages.

13. A method as set forth in claim 1 further comprising the step of washing the precipitated crystals in an aqueous solution of the arylamine salt of the perfluorocarbonic acid or its mixture with another strong acid with a pKa value below 2.5.

14. A method as set forth in claim 13 wherein said crystallization and washing steps are performed in several stages.

15. A method as set forth in claim 5 or 6 wherein a selected degree of protonization is obtained by extracting non protonized arylamine by means of hydrophobic solvents before the crystallization takes place.

16. A method for the simultaneous production of 4,4'-methylene diarylamine and polyamines which comprises the steps of condensing formaldehyde with a highly protonized aniline salt solution containing an acid catalyst at least of perfluoro-carbonic acid, eventually in a mixture with a strong acid having a pKa value of below 2.5, in a condensation chamber to obtain a homogeneous aqueous solution;

cooling the homogeneous solution in a temperature range of from 0° C. to 80° C. to crystallize and precipitate 4,4'-methylene diarylamine as a salt;

thereafter passing the crystallized salt into an exchange with aniline with the addition of water to obtain pure 4,4'-methylene aniline and an aqueous solution of aniline salts containing the acid radicals of the acid catalyst;

simultaneously passing separately the residual liquid of the crystallization into an exchange with aniline with the addition of water to obtain polyamines containing methylene bridges and an aqueous solution of aniline salts containing the acid radicals of the acid catalyst;

and thereafter concentrating and recycling both of the obtained aqueous aniline salt solutions to the condensation chamber.

* * * * *

UNITED STATES PATENT AND TRADEMARK OFFICE
CERTIFICATE OF CORRECTION

PATENT NO. : 4,297,511
DATED : October 27, 1981
INVENTOR(S) : Efim Biller

It is certified that error appears in the above—identified patent and that said Letters Patent is hereby corrected as shown below:

Column 5, line 39, after "B" insert --C--

Signed and Sealed this

Twenty-third Day of February 1982

[SEAL]

Attest:

GERALD J. MOSSINGHOFF

*Attesting Officer*   Commissioner of Patents and Trademarks